(12) United States Patent
Hallen

(10) Patent No.: US 12,622,812 B2
(45) Date of Patent: May 12, 2026

(54) OTOLOGICAL SURGERY UNDER PERFLUOROCARBON LIQUIDS

(71) Applicant: Alcon Inc., Fribourg (CH)

(72) Inventor: Paul R. Hallen, Colleyville, TX (US)

(73) Assignee: Alcon Inc., Fribourg (CH)

( * ) Notice: Subject to any disclaimer, the term of this patent is extended or adjusted under 35 U.S.C. 154(b) by 773 days.

(21) Appl. No.: 17/823,991

(22) Filed: Sep. 1, 2022

(65) Prior Publication Data

US 2023/0098216 A1     Mar. 30, 2023

Related U.S. Application Data

(60) Provisional application No. 63/249,123, filed on Sep. 28, 2021.

(51) Int. Cl.
| | |
|---|---|
| *A61F 11/20* | (2022.01) |
| *A61K 9/00* | (2006.01) |
| *A61K 31/02* | (2006.01) |

(52) U.S. Cl.
CPC .......... *A61F 11/202* (2022.01); *A61K 9/0024* (2013.01); *A61K 9/0046* (2013.01); *A61K 31/02* (2013.01)

(58) Field of Classification Search
CPC .......... A61F 11/202; A61F 11/20; A61F 2/18; A61F 2002/183; A61K 9/0024; A61K 9/0046; A61K 31/02; A61B 1/227; A61M 1/77; A61M 2202/0468; A61M 2210/0662
See application file for complete search history.

(56) References Cited

U.S. PATENT DOCUMENTS

| | | | |
|---|---|---|---|
| 5,409,904 A | 4/1995 | Hecht | |
| 6,290,690 B1 | 9/2001 | Huculak | |
| 6,632,423 B2 | 10/2003 | Jafari et al. | |
| 7,363,928 B2 | 4/2008 | Shah | |
| 7,820,194 B2 | 10/2010 | Jafari et al. | |
| 8,109,937 B2 | 2/2012 | Huculak et al. | |
| 9,119,859 B2 | 9/2015 | Stroman et al. | |
| 2012/0171281 A1* | 7/2012 | Spakevicius | A61K 9/127 514/743 |
| 2013/0095071 A1* | 4/2013 | Bance | A61K 9/0046 424/93.2 |
| 2021/0052428 A1* | 2/2021 | Black | A61F 11/202 |
| 2021/0138069 A1* | 5/2021 | Savel | A61K 31/4535 |
| 2023/0157896 A1* | 5/2023 | Gross | A61F 11/20 623/10 |
| 2024/0245602 A1* | 7/2024 | Pavlichenko | A61K 9/06 |

FOREIGN PATENT DOCUMENTS

| | | | | |
|---|---|---|---|---|
| WO | WO-2021183057 A1 * | 9/2021 | ............. | A61B 1/227 |
| WO | WO-2022047234 A1 * | 3/2022 | ............. | A61K 9/06 |

* cited by examiner

*Primary Examiner* — Ankit D Tejani
*Assistant Examiner* — Joshua Brendon Solomon

(57) ABSTRACT

Certain embodiments described herein provide a method of performing an otological surgical procedure including surgically accessing a middle ear, injecting a perfluorocarbon liquid into the middle ear, and suctioning the isolated blood from the middle ear without removing the perfluorocarbon liquid. The perfluorocarbon liquid is immiscible with blood for isolating blood in the middle ear from the perfluorocarbon liquid. In certain embodiments, the perfluorocarbon liquid has a specific gravity greater than blood to apply positive pressure to surrounding tissues. In certain embodiments, the method includes suctioning the perfluorocarbon liquid from the middle ear after the isolated blood is removed.

17 Claims, 8 Drawing Sheets

OTOLOGICAL SURGERY UNDER PERFLUOROCARBON LIQUIDS

PRIORITY CLAIM

This application claims the benefit of priority of U.S. Provisional Patent Application Ser. No. 63/249,123 titled "OTOLOGICAL SURGERY UNDER PERFLUOROCARBON LIQUIDS," filed on Sep. 28, 2021, whose inventor is Paul R. Hallen, which is hereby incorporated by reference in its entirety as though fully and completely set forth herein.

BACKGROUND

There are many conditions that affect the middle ear and require surgical intervention (referred to as "otological surgery"). For example, tympanoplasty is an otological surgical procedure performed to repair a perforated tympanic membrane. Stapendectomy is another example otological surgical procedure performed to remove all or part of the stapes bone and replace it with an artificial device. Adequate visualization is needed to perform many types of otological surgical procedures in addition to the above examples.

Current otological surgery techniques access the middle ear in one of two ways. One option is to remove the mastoid bone and visualize the middle ear using a microscope. A drawback of the first option is that removal of the mastoid bone is a very invasive procedure. A second option is to use an endoscope inserted into the ear canal to visualize the middle ear, however the endoscope can interfere with insertion and manipulation of other instruments.

With either option, blood that is present in the middle ear during surgery further interferes with visualization. Current otological surgery techniques are performed under air and are unable to adequately prevent bleeding, hold back tissues, and isolate the blood to improve visualization. Use of diathermy to induce clotting is challenging because the source of bleeding is often unknown.

Thus, there is a need in the art for improved fluids and/or surgical methods that address at least some of the issues described above.

BRIEF SUMMARY

The present disclosure relates generally to fluids used in otological surgery and surgical procedures associated with the use of such fluids.

Certain embodiments described herein provide a method of performing an otological surgical procedure including surgically accessing a middle ear, injecting a perfluorocarbon liquid into the middle ear, and suctioning the isolated blood from the middle ear without removing the perfluorocarbon liquid. The perfluorocarbon liquid is immiscible with blood for isolating blood in the middle ear from the perfluorocarbon liquid. In certain embodiments, the perfluorocarbon liquid has a specific gravity greater than blood to apply positive pressure to surrounding tissues. In certain embodiments, the method includes suctioning the perfluorocarbon liquid from the middle ear after the isolated blood is removed.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

FIGS. 3A-3E illustrate chemical structures of example perfluorocarbon liquids, according to certain embodiments To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Aspects of the present disclosure provide fluids for use in otological surgery and surgical procedures associated with the use of such fluids.

As described above, current otological surgery techniques are performed under air and are unable to adequately prevent bleeding, hold back tissues, and isolate the blood to improve visualization. Particular embodiments described in the present disclosure overcome these deficiencies by providing improved fluids and/or surgical methods for improving visualization.

Certain embodiments disclosed herein provide fluids that are heavy (e.g., higher molecular weight or specific gravity) compared to water and blood for applying pressure to stop bleeding and holding back or flattening tissues in the ear to improve visualization of and/or access to a surgical target. Certain embodiments disclosed herein provide fluids that are less viscous compared to water and blood to enable the fluid to conform to the shape of the middle ear. Certain embodiments disclosed herein provide fluids that are translucent and/or transparent to enable visualization of a surgical target through the fluid. Certain embodiments disclosed herein provide fluids that are immiscible with blood for isolating or separating blood from the fluid and enabling the surgeon to remove the isolated blood to improve visualization of a surgical target.

Figure 1:
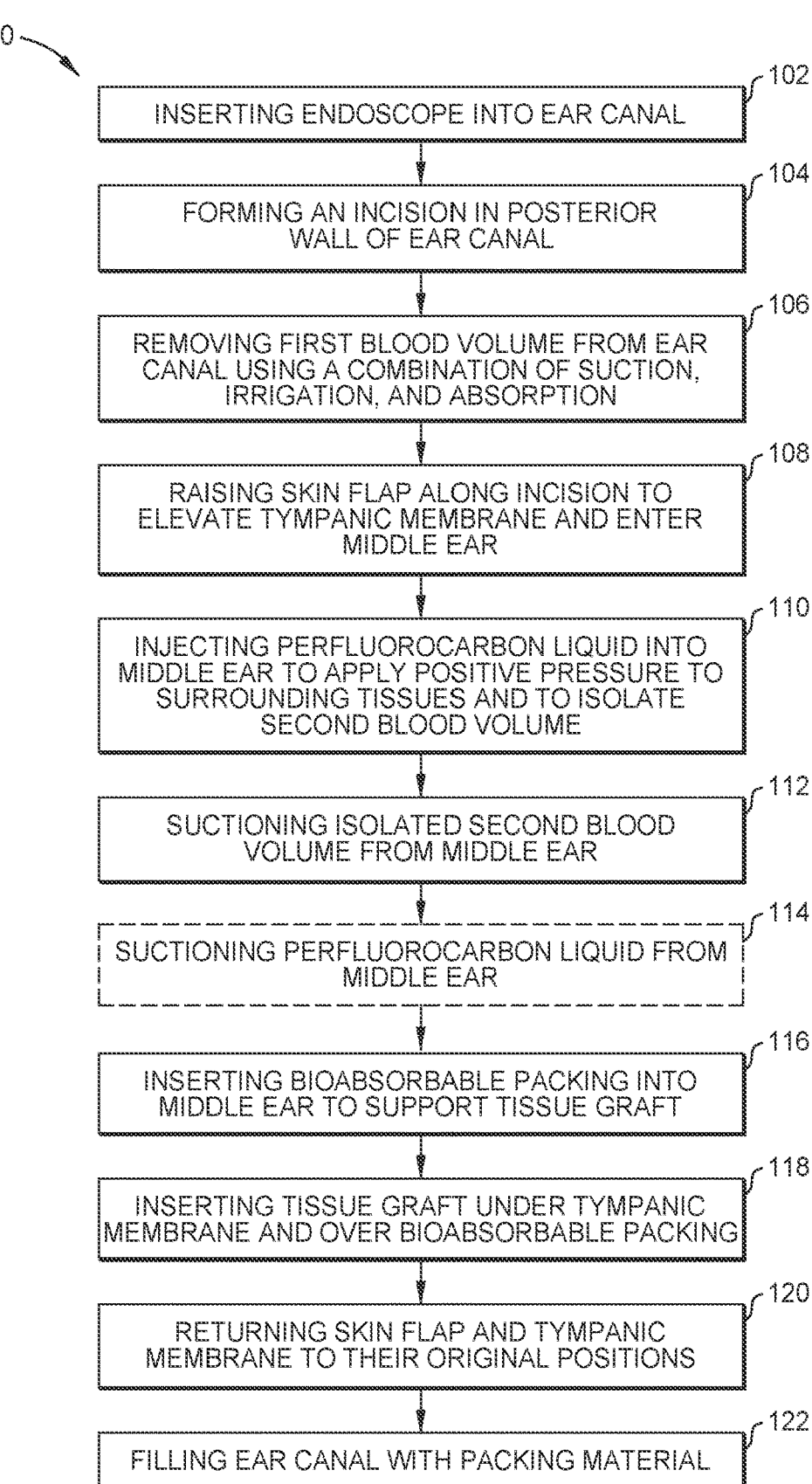
FIG. 1 illustrates an example otological surgical procedure using fluids described herein, according to certain embodiments.

FIG. 1 illustrates an example otological surgical procedure. The example procedure illustrated in FIG. 1 is a medial tympanoplasty procedure 100 to repair a perforated tympanic membrane. In medial tympanoplasty, a tissue graft is placed medial to the tympanic membrane as described in detail below. FIGS. 2A-2K schematically illustrate the ear 200 at each stage of procedure 100. FIG. 1 and FIGS. 2A-2K are, therefore, described together herein for clarity.

Figure 2A:
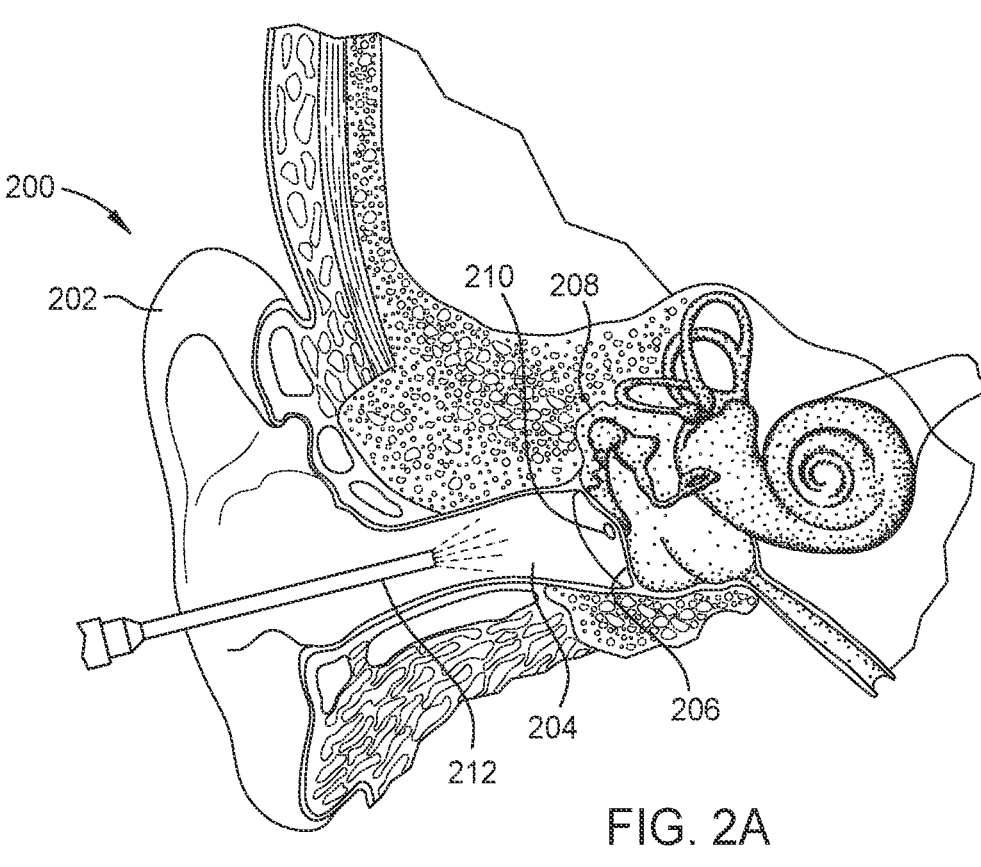
FIGS. 2A-2K schematically illustrate the ear at each stage of the procedure of FIG. 1, according to certain embodiments.

As shown in FIG. 2A, ear 200 generally includes auricle 202 (also referred to as "outer ear"), external acoustic meatus 204 (also referred to as "ear canal"), tympanic membrane 206 (also referred to as "ear drum"), and tympanic cavity 208 (also referred to as "middle ear"). In the illustrated example, tympanic membrane 206 has a small, round perforation 210, which is located near a radial center of tympanic membrane 206. However, the size, shape, and location of perforation 210 is for illustrative purposes only. In other examples, perforation 210 may have a different shape, may be larger or smaller than illustrated, and may be located anywhere on tympanic membrane 206. As shown in FIG. 2A, at operation 102, an endoscope 212 is inserted into ear canal 204. In certain embodiments, endoscope 212 provides real-time imaging inside ear canal 204 to enable the surgeon to visualize tympanic membrane 206 and perforation 210. Although endoscope 212 is disposed in ear canal 204 throughout procedure 100, endoscope 212 is omitted from FIGS. 2B-2K for clarity.

Figure 2B:
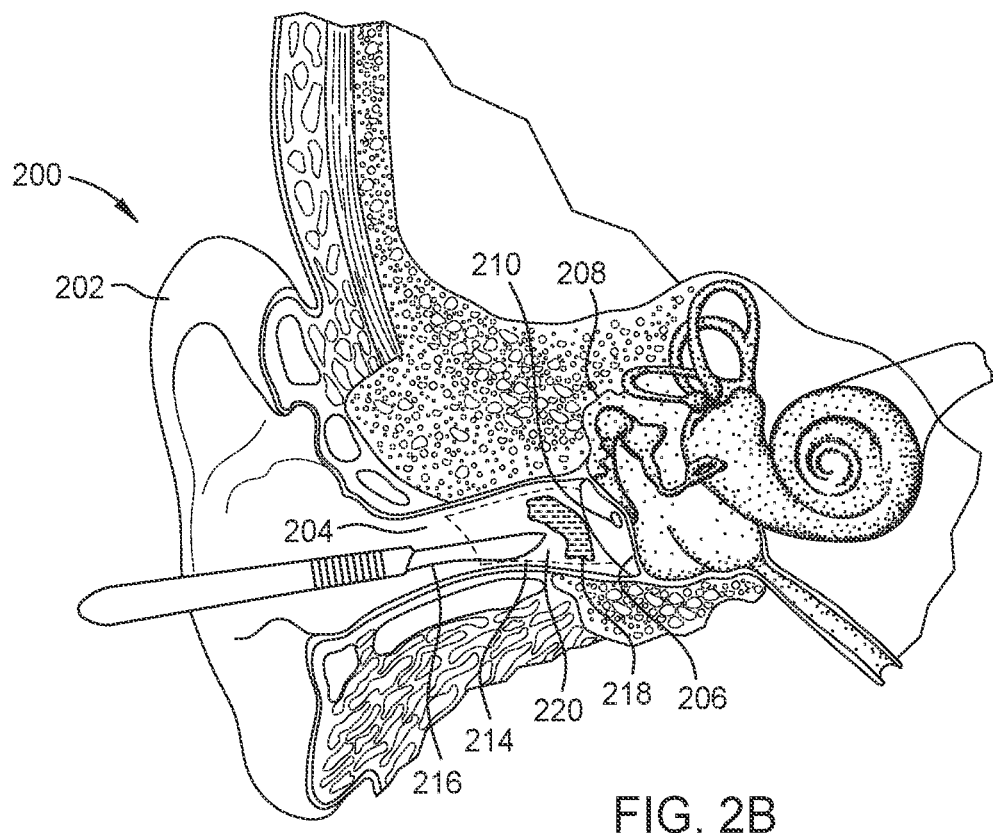

As shown in FIG. 2B, at operation 104, an incision 214 is created in a posterior wall of ear canal 204. In other examples, ear canal 204 may be incised along an anterior, superior, or inferior wall. In the illustrated embodiments, the surgeon uses a scalpel 216 to dissect one or more layers of tissue lining ear canal 204. In other examples, alternative methods of tissue dissection may be used to create incision 214. Bleeding from the dissected tissues causes at least partial filling of ear canal 204 with a first blood volume 218. First blood volume 218 is illustrated as filling an isolated region of ear canal 204 for illustrative purposes only. In some examples, first blood volume 218 may mix with other fluids, diffuse substantially throughout ear canal 204, contact tympanic membrane 206, and/or leak into middle ear 208. A skin flap 220 is formed in the wall of ear canal 204. Skin flap 220 is defined within an area bordered by incision 214. As shown in the illustrated embodiments, medial ends of incision 214 adjoin tympanic membrane 206. In other embodiments, incision 214 is spaced from and not in contact with tympanic membrane 206 to avoid damaging tympanic membrane 206 during creation of incision 214.

Figure 2C:
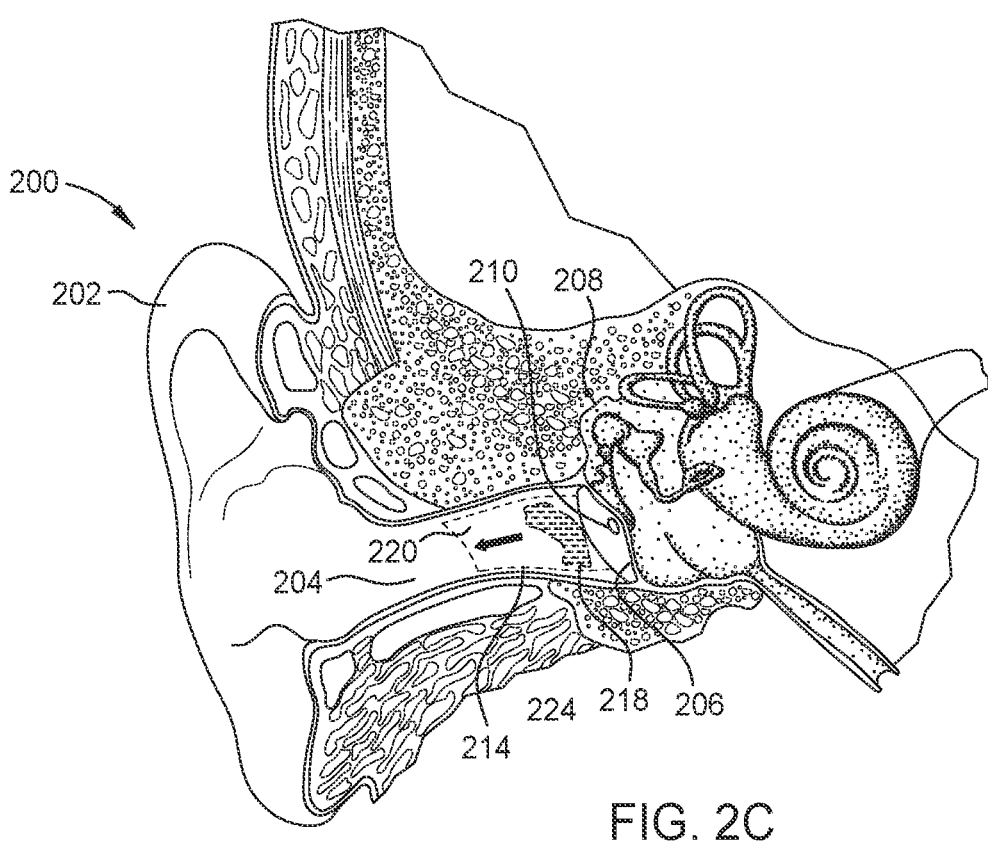

As shown in FIG. 2C, at operation 106, first blood volume 218 is removed from ear canal 204 using a combination of suction, irrigation, and absorption. In certain embodiments, saline irrigation is used to wash ear canal 204. In certain embodiments, epinephrine-soaked absorbent pads (also referred to as "pledgets") are used to absorb first blood volume 218 and to help stop bleeding from incision 214.

Figure 2D:
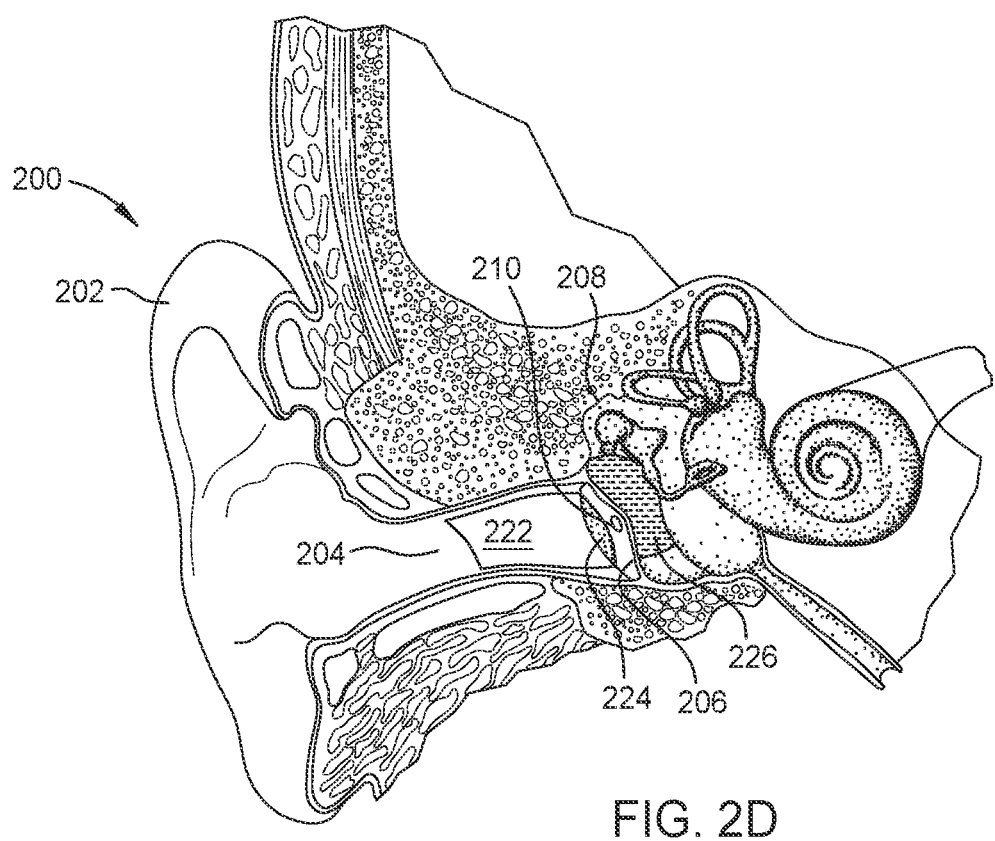

As shown in FIG. 2D, at operation 108, skin flap 220 (shown in FIG. 2B) is raised along incision 214 to elevate tympanic membrane 206 and enter middle ear 208. In FIG. 2D, an area of exposed tissue 222 underneath skin flap 220 is shown, whereas skin flap 220 itself is omitted for clarity. Through elevation of tympanic membrane 206, an opening 224 is formed between a backside of skin flap 220 and a front side of exposed tissue 222. Opening 224 provides fluid communication between ear canal 204 and middle ear 208. Bleeding that occurs due to raising skin flap 220 and elevating tympanic membrane 206 causes at least partial filling of middle ear 208 with a second blood volume 226. Second blood volume 226 is illustrated as filling an isolated region of middle ear 208 for illustrative purposes only. In some examples, second blood volume 226 may mix with other fluids, diffuse substantially throughout middle ear 208, contact tympanic membrane 206, and/or leak into ear canal 204. In certain embodiments, second blood volume 226 interferes with visualization of the surgical target.

Figure 2E:
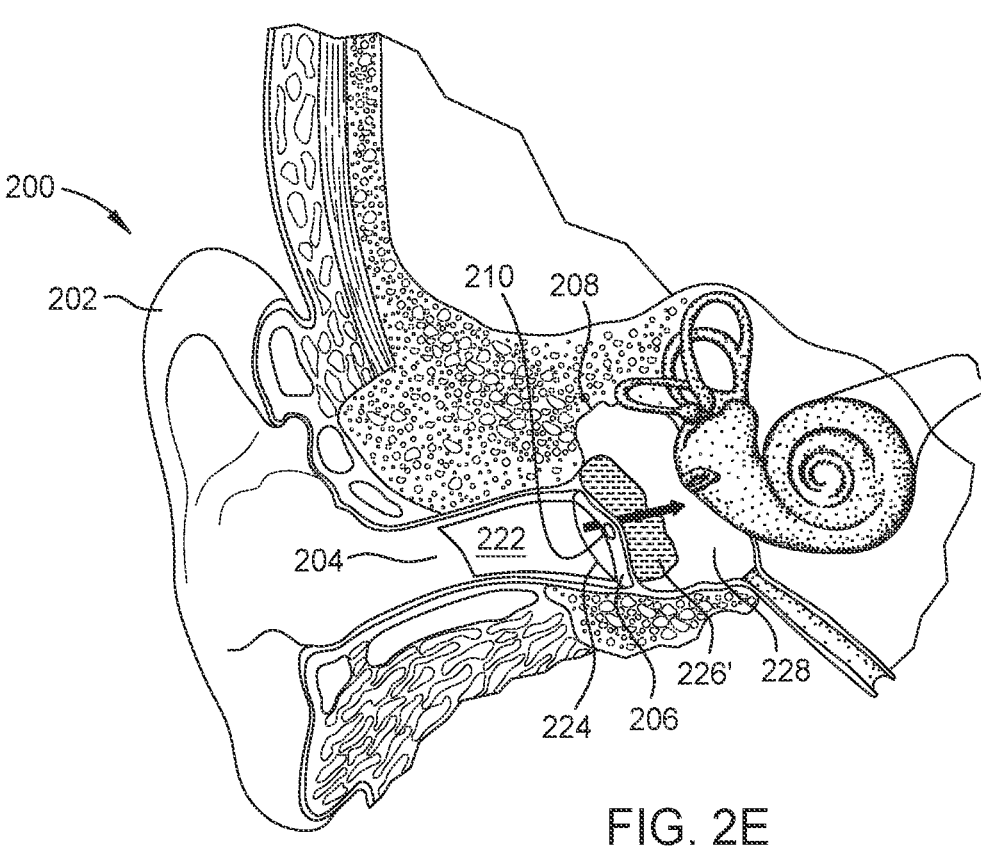

As shown in FIG. 2E, at operation 110, a perfluorocarbon liquid (PFCL) 228 is injected into middle ear 208 to apply positive pressure to surrounding tissues and to isolate second blood volume (shown as 226'). In certain embodiments, perfluorocarbon liquid 228 is injected through opening 224. In certain embodiments, application of positive pressure by perfluorocarbon liquid 228 helps stop bleeding and hold back or flatten the surrounding tissues. In certain embodiments, a volume of perfluorocarbon liquid 228 injected into middle ear 208 substantially displaces air in order to enable perfluorocarbon liquid 228 to conform to the shape of middle ear 208 and uniformly apply pressure to stop bleeding and hold back tissues on all sides. In some other embodiments, a volume of perfluorocarbon liquid 228 injected into middle ear 208 only partially displaces air.

In certain embodiments, the volume of perfluorocarbon liquid 228 injected into middle ear 208 is about equal to the total volume of middle ear 208. In such embodiments, the volume of perfluorocarbon liquid 228 is about 0.5 cc (cubic centimeters) to about 1 cc. In some other embodiments, a ratio of the volume of perfluorocarbon liquid 228 injected to the total volume of middle ear 208 is about 0.1 to about 1, such as about 0.3 to about 1, such as about 0.5 to about 1, such as about 0.7 to about 1, such as about 0.8 to about 1, such as about 0.9 to about 1, or about 0.3 to about 0.9, such as about 0.5 to about 0.8, such as about 0.7, or about 0.1 to about 0.2, about 0.2 to about 0.3, about 0.3 to about 0.4, about 0.4 to about 0.5, about 0.5 to about 0.6, about 0.6 to about 0.7, about 0.7 to about 0.8, about 0.8 to about 0.9, or about 0.9 to about 1. In some other embodiments, the volume of perfluorocarbon liquid 228 injected into middle ear 208 is about 0.05 cc to about 1 cc, such as about 0.15 cc to about 0.9 cc, such as about 0.25 cc to about 0.8 cc, such as about 0.35 cc to about 0.7 cc, such as about 0.35 cc or about 0.7 cc, or about 0.1 cc to about 0.2 cc, about 0.2 cc to about 0.3 cc, about 0.3 cc to about 0.4 cc, about 0.4 cc to about 0.5 cc, about 0.5 cc to about 0.6 cc, about 0.6 cc to about 0.7 cc, about 0.7 cc to about 0.8 cc, about 0.8 cc to about 0.9 cc, or about 0.9 cc to about 1 cc.

Figures 3A, 3B, 3C, 3D, 3E:
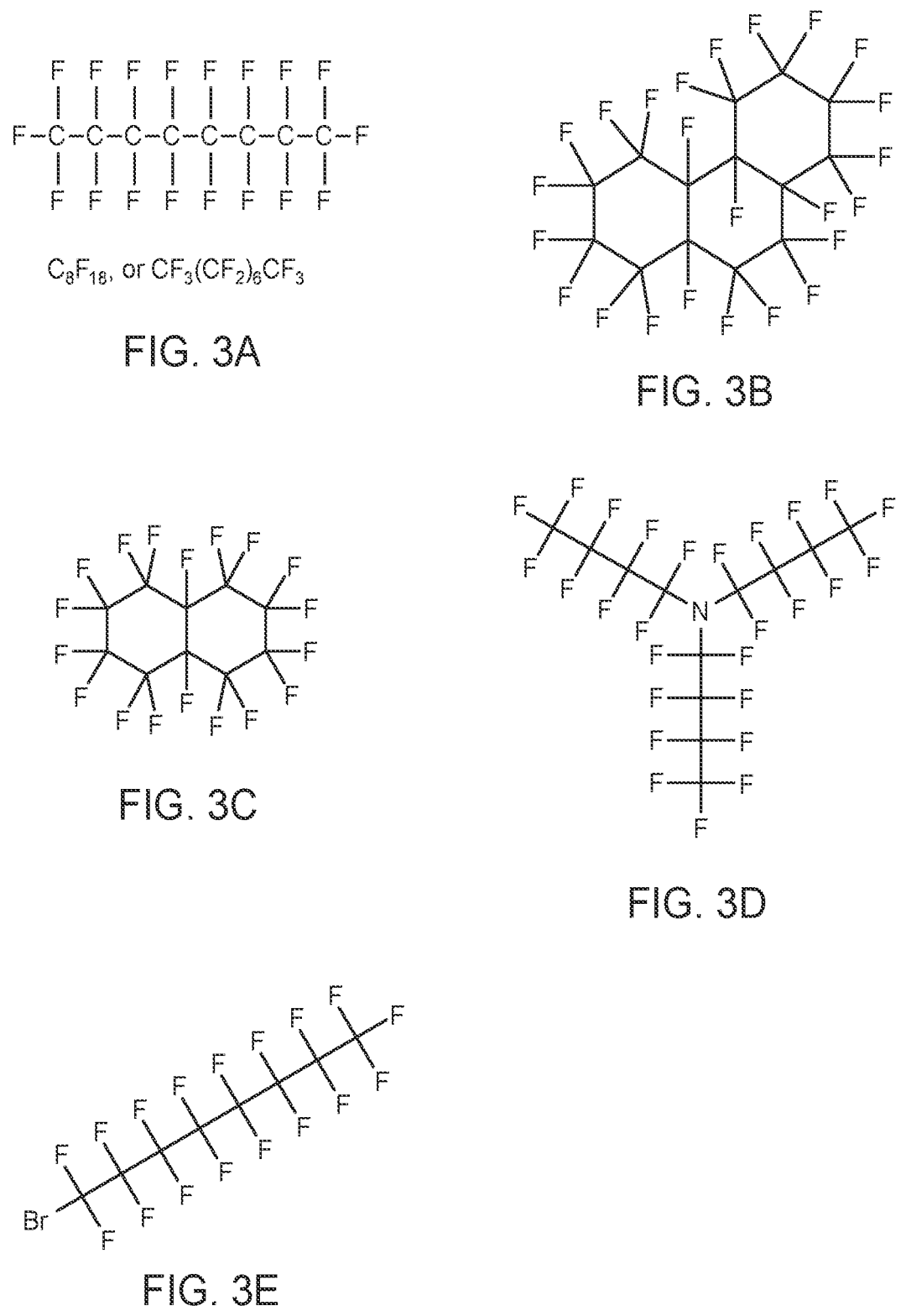

Chemical structures of example perfluorocarbon liquids are illustrated in FIGS. 3A-3E. Certain non-limiting examples of perfluorocarbon liquids of the present disclosure include perfluoro-n-octane (also referred to as "Perfluoron®") (FIG. 3A), perfluoroperhydrophenanthrene (also referred to as "Vitreon®") (FIG. 3B), perfluorodecalin (PFD) (FIG. 3C), perfluorotributylamide (PFTB) (FIG. 3D), or perfluorooctylbromide (PFOB) (FIG. 3E). In the present disclosure, perfluorocarbon liquids are purified to have a perfluorocarbon concentration of at least 99% v/v (volume per volume) or greater. In certain embodiments, the perfluorocarbon concentration is greater than about 99.9% v/v.

In certain embodiments, perfluorocarbon liquids of the present disclosure have a higher molecular weight than blood. In some embodiments, perfluorocarbon liquid molecular weight is greater than about 400 g/mol (grams per mole), such as about 400 g/mol to about 600 g/mol. In one example, the molecular weight of perfluoro-n-octane is 438 g/mol. In some embodiments, the perfluorocarbon liquids have a higher specific gravity than blood. In certain embodiments, the specific gravity is greater than about 1.5 g/cc (gram per cubic centimeter) at 25° C. (Celsius), such as about 1.5 g/cc to about 2.0 g/cc at 25° C. In one example, the specific gravity of perfluoro-n-octane is approximately 1.754 g/cc at 25° C. Beneficially, the higher molecular weight and/or higher specific gravity of the perfluorocarbon liquids compared to blood applies positive pressure to surrounding tissues to stop bleeding and hold back tissues in the ear to improve visualization of and/or access to a surgical target.

In certain embodiments, perfluorocarbon liquids of the present disclosure have a lower viscosity than blood, which enables the perfluorocarbon liquids to conform to the shape of the middle ear. In certain embodiments, perfluorocarbon liquid viscosity is less than about 0.8 centistokes at 25° C., such as about 0.6 centistokes to about 0.8 centistokes at 25° C. In one example, the viscosity of perfluoro-n-octane is approximately 0.69 centistokes at 25° C.

In certain embodiments, perfluorocarbon liquids of the present disclosure are optically clear to enable visualization of a surgical target through the perfluorocarbon liquids. In some embodiments, the perfluorocarbon liquids have a refractive index similar to water. In certain embodiments, perfluorocarbon liquid refractive index is about 1.2 to about 1.4, such as about 1.33. In one example, the refractive index of perfluoro-n-octane is approximately 1.27.

In certain embodiments, perfluorocarbon liquids of the present disclosure are immiscible with blood for isolating or separating blood from the fluid and enabling the surgeon to remove the isolated blood to improve visualization of a surgical target.

Figure 2F:
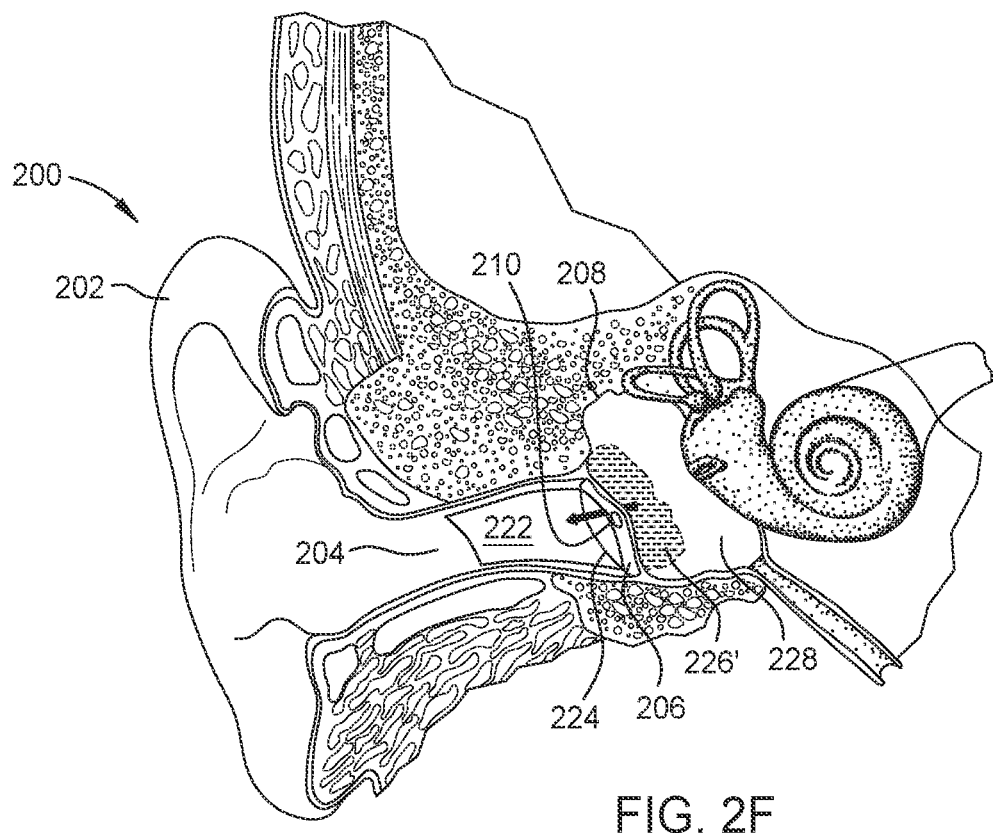

As shown in FIG. 2F, at operation 112, isolated second blood volume 226' is suctioned from middle ear 208. In certain embodiments, isolated second blood volume 226' is removed through opening 224. Isolated second blood volume 226' is removed from middle ear 208 without removing perfluorocarbon liquid 228. In certain embodiments, isolated second blood volume 226' is removed without irrigation or absorption, in contrast to removal of first blood volume 218 from ear canal 204 at operation 106 as described above. Because middle ear 208 is at least partially filled with perfluorocarbon liquid 228 during removal of isolated second blood volume 226', concurrent refilling of middle ear 208 with air and/or additional blood is reduced or prevented. Therefore, maintaining perfluorocarbon liquid 228 in middle ear 208 when isolated second blood volume 226' is removed helps control bleeding and provides resistance to surrounding tissues while also improving visualization.

Figure 2G:
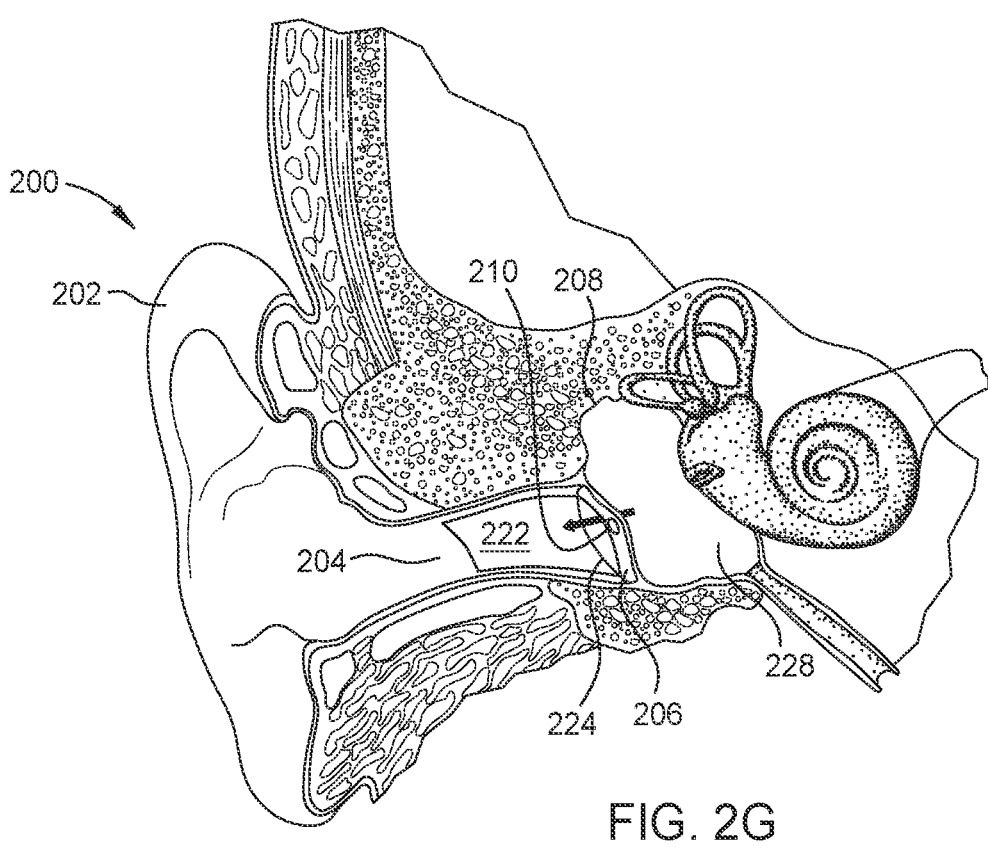

As shown in FIG. 2G, at operation 114, perfluorocarbon liquid 228 is suctioned from middle ear 208. In certain embodiments, perfluorocarbon liquid 228 is removed through opening 224. In the illustrated embodiments, perfluorocarbon liquid 228 is removed after suctioning isolated second blood volume 226' from middle ear 208. However, operations of procedure 100 may be performed in a different order from that shown. For example, perfluorocarbon liquid 228 may be removed after operation 116 (FIG. 2H) or operation 118 (FIG. 2I), which are described in detail below. In some other embodiments, perfluorocarbon liquid 228 remains in middle ear 208 throughout procedure 100. In such embodiments, perfluorocarbon liquid 228 may be absorbed naturally by the body, drain out of middle ear 208 without subsequent intervention, or be removed by the surgeon in a follow-up procedure. Leaving perfluorocarbon liquid 228 in middle ear 208 throughout procedure 100 may help control bleeding and reducing tissue swelling within middle ear 208.

Figure 2H:
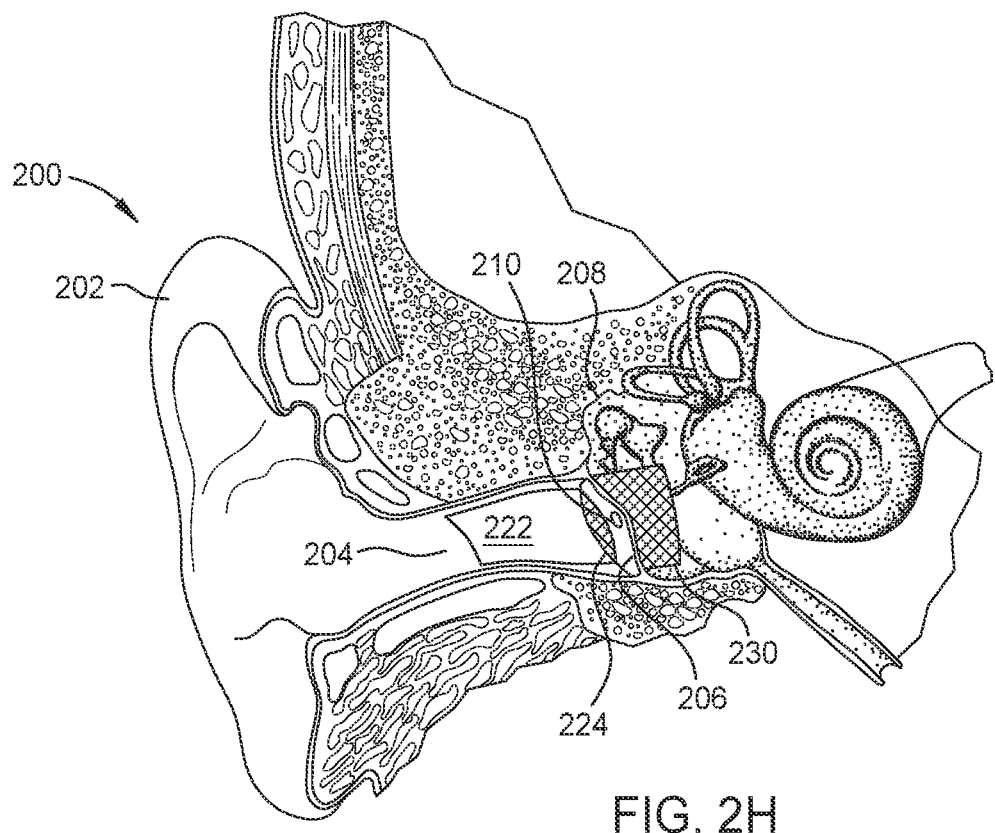
Figure 2I:
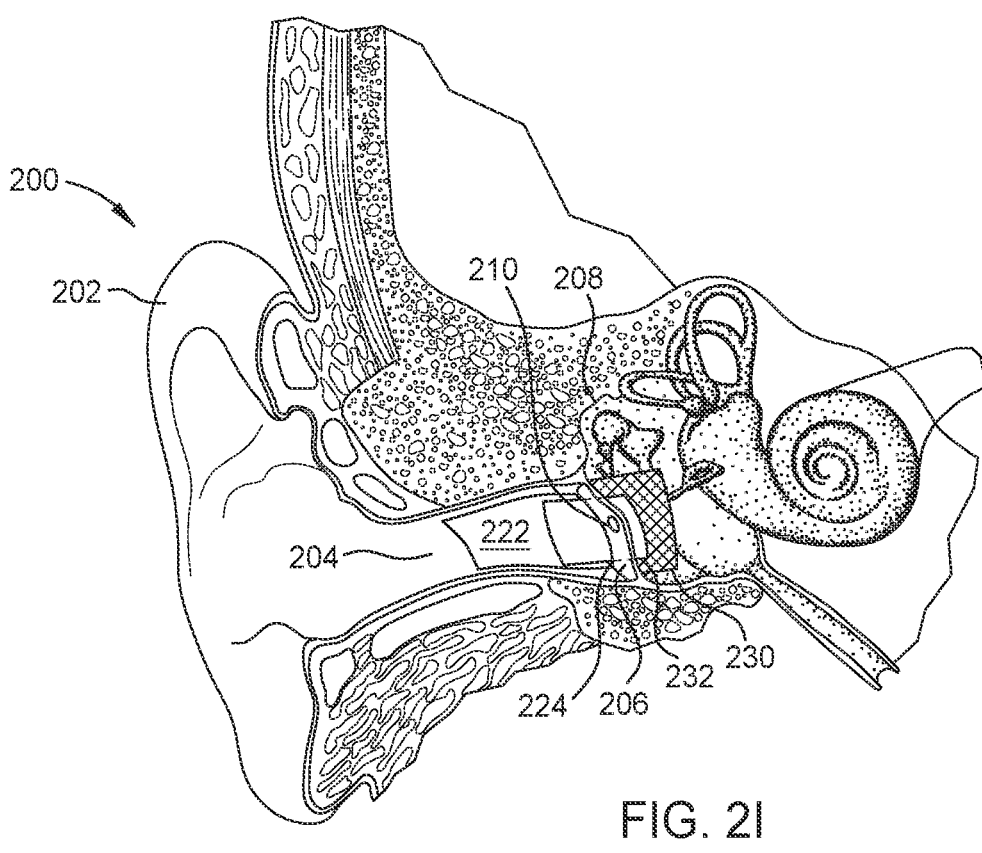

As shown in FIG. 2H, at operation 116, bioabsorbable packing 230 is inserted into middle ear 208 to support a tissue graft 232 (shown in FIG. 2I). In some embodiments, bioabsorbable packing 230 includes sponges formed from gelatin (e.g., Gelfoam®). Bioabsorbable packing 230 is inserted through opening 224 and provides physical support to help position tissue graft 232 during healing.

As shown in FIG. 2I, at operation 118, tissue graft 232 is inserted under tympanic membrane 206 and over bioabsorbable packing 230. Tissue graft 232 is inserted through opening 224 (referred to as an "underlay technique"). Tissue graft 232 is disposed at least partially in middle ear 208. Tissue graft 232 is positioned to entirely cover perforation 210. Support from bioabsorbable packing 230 underneath tissue graft 232 keeps tissue graft 232 in close contact with a medial wall of tympanic membrane 206 to promote healing.

Figure 2J:
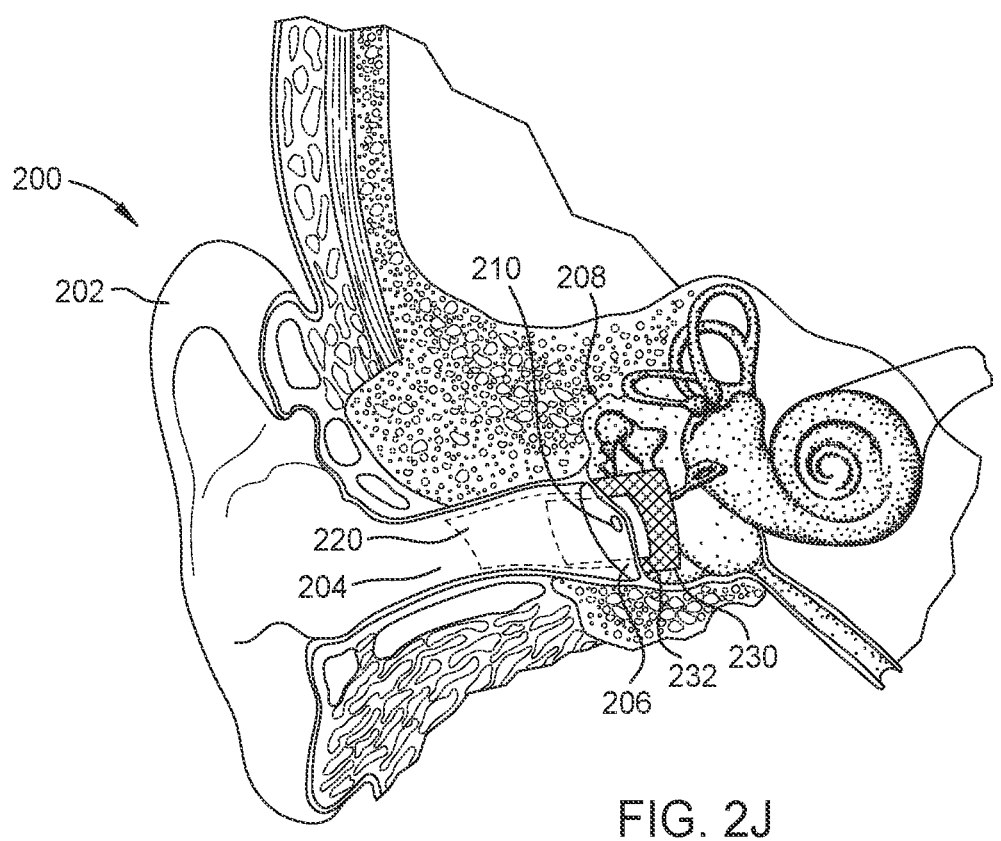

As shown in FIG. 2J, at operation 120, skin flap 220 and tympanic membrane 206 are returned to their original positions. As indicated by the dashed line, tissue graft 232 is disposed at least partially between the backside of skin flap 220 and the front side of exposed tissue 222. In the original position, skin flap 220 entirely covers exposed tissue 222.

Figure 2K:
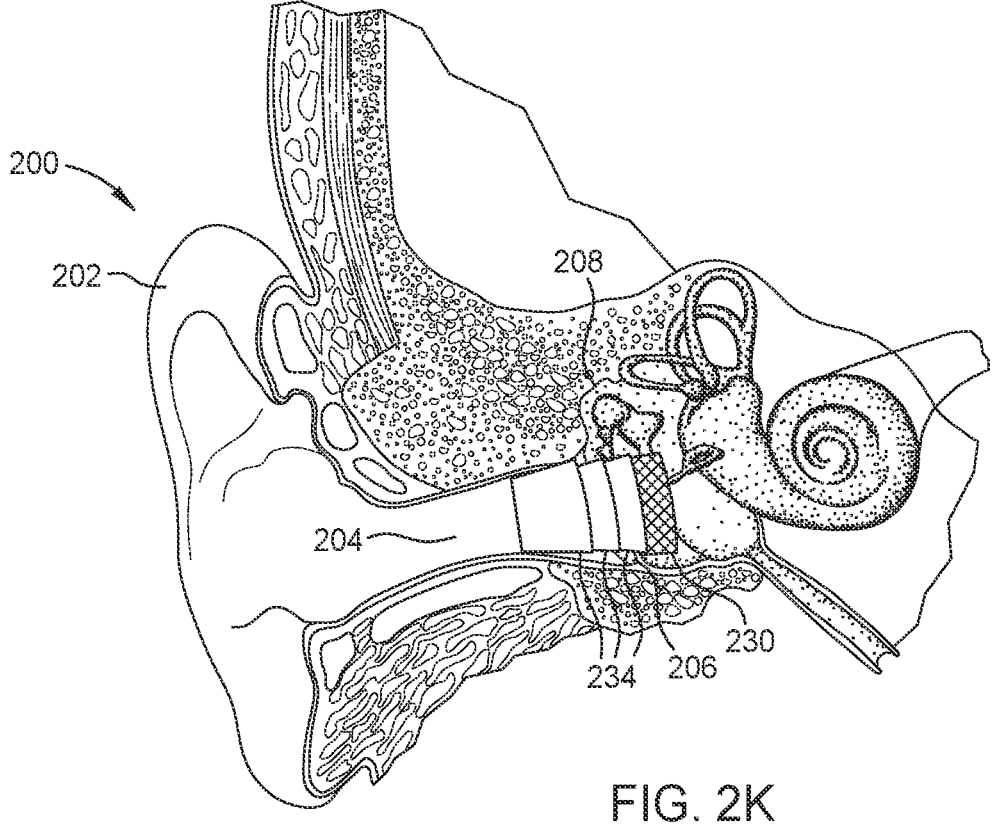

As shown in FIG. 2K, at operation 122, ear canal 204 is filled with packing material 234. Excess packing material 234 disposed on a lateral side of tympanic membrane 206 helps maintain skin flap 220 and tympanic membrane 206 in their original positions during post-operative healing. In certain embodiments, packing material 234 includes non-absorbable gauze that is removed during a follow-up procedure. In other embodiments, packing material 234 is bioabsorbable.

As described above, FIG. 1 and FIGS. 2A-2K illustrate perfluorocarbon liquid injection into the middle ear during a medial tympanoplasty procedure performed via the ear canal. However, other medial tympanoplasty procedures may be performed through removal of the mastoid bone. In such examples, perfluorocarbon liquid injection may be performed after removal of the mastoid bone and before placement of the tissue graft to help control bleeding, improve visualization, or both. Perfluorocarbon liquid injection may be indicated for use in numerous other otological surgical procedures involving the middle ear or inner ear including, for example, stapendectomy, cochlear implantation, myringotomy, and other tympanoplasty procedures, such as lateral tympanoplasty as described below.

Lateral tympanoplasty involves functional replacement of the entire tympanic membrane. In lateral tympanoplasty, the ear canal is widened to create a bony shelf for placement of a tissue graft lateral to the position of the tympanic membrane. In lateral tympanoplasty, some or most of the tympanic membrane is removed prior to placing the tissue graft. In lateral tympanoplasty, bleeding occurs as a result of widening the ear canal and removal of the tympanic membrane causing at least partial filling of the middle ear with blood. Thus, lateral tympanoplasty procedures are able to benefit from improved visualization achieved through injection of perfluorocarbon liquids into the middle ear and subsequent suction of isolated blood as described above.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. A method of performing a medial tympanoplasty surgical procedure, comprising:
   surgically accessing a middle ear by making an incision in a wall of an ear canal;
   raising a skin flap along the incision to enter the middle ear;
   injecting a perfluorocarbon liquid into the middle ear, the perfluorocarbon liquid is immiscible with blood for isolating blood, in the middle ear from the incision, from the perfluorocarbon liquid; and
   suctioning the isolated blood from the middle ear without removing the perfluorocarbon liquid.

2. The method of claim 1, wherein the perfluorocarbon liquid has a specific gravity greater than blood to apply positive pressure to surrounding tissues.

3. The method of claim 1, further comprising suctioning the perfluorocarbon liquid from the middle ear after the isolated blood is removed.

4. The method of claim 3, further comprising inserting bioabsorbable packing into the middle ear before suctioning the perfluorocarbon liquid from the middle ear.

5. The method of claim 1, wherein the perfluorocarbon liquid comprises at least one of perfluoro-n-octane, perfluoroperhydrophenanthrene, perfluorodecalin, perfluorotributylamide, or perfluorooctylbromide.

6. The method of claim 5, wherein the perfluorocarbon liquid comprises perfluoro-n-octane.

7. The method of claim 1, wherein the perfluorocarbon liquid has a viscosity less than blood to enable the perfluorocarbon liquid to conform to a shape of the middle ear.

8. The method of claim 7, wherein the viscosity is less than about 0.8 centistokes at 25° C.

9. The method of claim 1, wherein a volume of the perfluorocarbon liquid injected into the middle ear is about equal to a total volume of the middle ear.

10. The method of claim 9, wherein the volume of the perfluorocarbon liquid injected into the middle ear is about 0.5 cc to about 1 cc.

11. The method of claim 1, wherein a ratio of a volume of the perfluorocarbon liquid injected into the middle ear to a total volume of the middle ear is about 0.5 to about 1.

12. The method of claim 1, wherein the perfluorocarbon liquid remains in the middle ear throughout the procedure.

13. The method of claim 12, wherein the perfluorocarbon liquid is removed from the middle ear in a follow-up procedure.

14. The method of claim 12, wherein the perfluorocarbon liquid is absorbed naturally by a human body.

15. The method of claim 1, further comprising inserting bioabsorbable packing into the middle ear.

16. The method of claim 15, further comprising inserting a tissue graft under a tympanic membrane and over the bioabsorbable packing.

17. The method of claim 16, further comprising filling the ear canal with packing material.

\* \* \* \* \*